United States Patent [19]

Legrand

[11] Patent Number: 4,736,619

[45] Date of Patent: Apr. 12, 1988

[54] DEVICE FOR MEASURING THE ALCOHOL CONTENT OF A GAS

[76] Inventor: Guy Legrand, 10, Boulevard Jourdan, 75014 Paris, France

[21] Appl. No.: 916,678

[22] PCT Filed: Feb. 14, 1986

[86] PCT No.: PCT/FR86/00046

§ 371 Date: Sep. 19, 1986

§ 102(e) Date: Sep. 19, 1986

[87] PCT Pub. No.: WO86/04992

PCT Pub. Date: Aug. 28, 1986

[30] Foreign Application Priority Data

Feb. 15, 1985 [FR] France .................. 85 02177

[51] Int. Cl.⁴ ............................................. G01N 1/14
[52] U.S. Cl. .............................................. 73/23; 422/84; 128/730
[58] Field of Search .................. 73/23, 864.62, 863.02; 128/719, 730; 422/84

[56] References Cited

U.S. PATENT DOCUMENTS

| | | | |
|---|---|---|---|
| 3,238,783 | 3/1966 | Wright | 73/864.62 |
| 3,764,270 | 10/1973 | Collier et al. | 422/84 |
| 4,132,109 | 1/1979 | Vandersyde | 73/23 |
| 4,248,245 | 2/1981 | Kempin | 128/719 |
| 4,297,871 | 11/1981 | Wright et al. | 73/23 |
| 4,298,010 | 11/1981 | Eckstein et al. | 128/719 |
| 4,346,584 | 8/1982 | Boehringer | 73/23 |
| 4,535,780 | 8/1985 | Gur et al. | 128/730 |
| 8,278,636 | 7/1981 | Voigt et al. | 128/719 |

FOREIGN PATENT DOCUMENTS 1443438  7/1976  United Kingdom ............ 73/23
2043892 10/1980  United Kingdom .

*Primary Examiner*—Stewart J. Levy
*Assistant Examiner*—Hezron E. Williams
*Attorney, Agent, or Firm*—Sughrue, Mion, Zinn, Macpeak & Seas

[57] ABSTRACT

A device for measuring the alcohol content of a gas includes an improved mechanism for determining the presence of alveolar air in the gas which is exhaled into the device by a test subject. The device has a conduit (11) into which the test subject exhales. Gas from the conduit passes through a nozzle (19) and into an intake opening (18) of a pumping device (14). Upon actuation, the pumping device extracts a first predetermined volume of exhaled air from the conduit, so that an electrochemical cell (25) can detect the quantity of alcohol in the first predetermined volume of air. To actuate the pumping device, a predetermined value correspondig to a second volume of air must be detected by an evaluation device (28) responsive to a pressure sensitive device (27) for measuring the pressure of the gas in the conduit. In addition, the pumping device will not be actuated until a threshold circuit (35) detects a minimum pressure.

12 Claims, 1 Drawing Sheet

U.S. Patent    Apr. 12, 1988    4,736,619
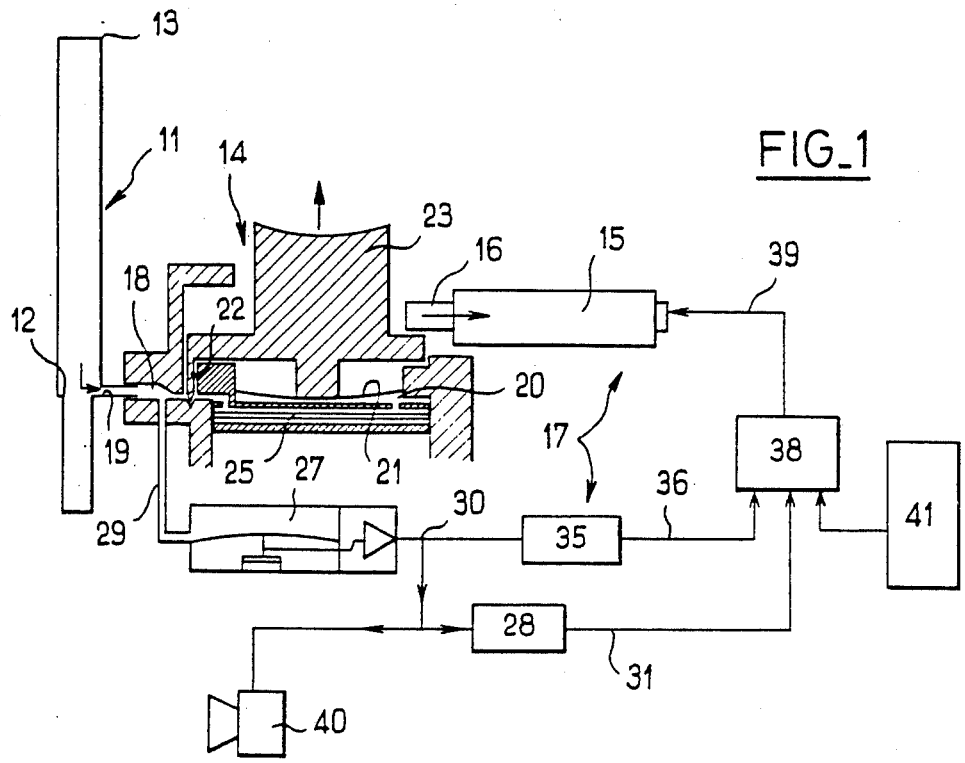
FIG_1
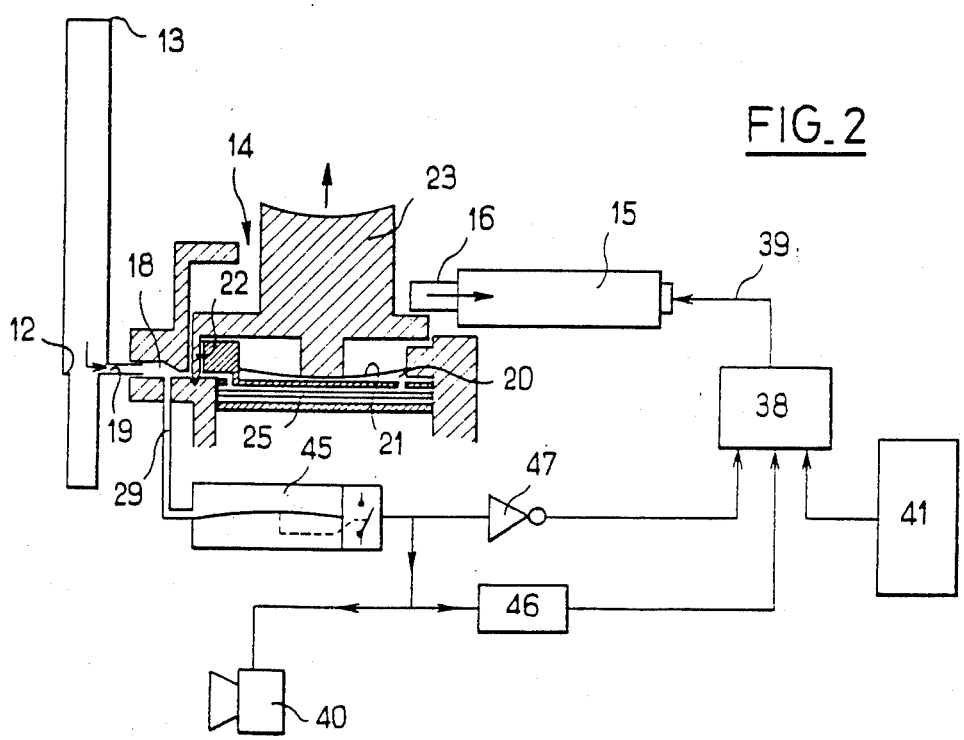
FIG_2

DEVICE FOR MEASURING THE ALCOHOL CONTENT OF A GAS

BACKGROUND OF THE INVENTION

The invention pertains to a device to analyze the alcohol content of a gas, especially for testing an automobilist's alcoholemia level; more specifically, it pertains to an arrangement of testing circuits which allow it to be ensured that exhaled air is taken under satisfactory conditions of reliability and precision.

It is known that, in order to ensure the reliability of an alcoholemia test, the air sample which is analyzed must come from the deepest part of the lungs: the term "alveolar air" is commonly used to designate the fraction of air which is discharged at the end of a complete exhalation period because it comes from the alveolar passages of the lungs. It is the analysis of the alcohol content of this "alveolar air" which allows the driver's alcoholemia level to be determined with sufficient precision.

Various devices are known which are intended to measure the alcohol content of a gas. For example, U.S. Pat. No. 4,346,584 describes an automatic analyzing device which takes a sample of gas at the end of the exhalation as soon as the pressure decreases in the intake conduit. French Pat. No. 2,449,877 describes a device for taking a breath sample, comprising a pressure sensor which controls the activation of a timing unit which delays the instant at which the measurement is taken. Nonetheless, these known devices do not provide a reliable measurement of the alcohol content of alveolar air under all circumstances.

SUMMARY OF THE INVENTION

One of the goals of the invention is to propose a device which can measure the alcohol content of air which is discharged at the end of an exhalation period of a subject being tested.

Another purpose of the invention is to propose such a device which can take a predetermined quantity of alveolar air, at the end of the exhalation period, regardless of the subject's thoracic capacity.

Another purpose of the invention is to propose such a device endowed with means to verify that the subject is continuously and fully exhaling air from his lungs, especially without again inhaling fresh air.

In this spirit, the invention pertains essentially to a device to analyze the alcohol content of a gas, especially to test an individual's alcoholemia level; this device is different in that it comprises a conduit (11) for the circulation of said gas, a controlled pumping device (14), connected to said conduit to take a predetermined volume of said gas when it is activated, with this pumping device being connected to means to detect and measure alcohol (25) and means (17) to control the activation of the pumping device comprising a cascade assembly of a device (27) which is sensitive to the pressure prevailing in said conduit and a device (28) to evaluate a volume of gas, controlled by said pressure sensitive device.

With such an arrangement, it is ensured that the air which is analyzed is taken towards the end of the exhalation period.

According to another important characteristic of the invention, the device also comprises means to detect a low threshold of the pressure prevailing in said conduit and logical means to link the signal issued by said evaluation means and the signal issued by said low threshold detection means, to formulate the control for the pumping system. Thus, with such a device, the air to be analyzed is taken only when a minimum amount of air has been exhaled and when the subject stops blowing into the conduit, with the pressure in the latter falling at that time to a value close to atmospheric pressure.

BRIEF DESCRIPTION OF THE DRAWINGS

The invention will emerge more clearly in light of the description below of two possible embodiments for a device according to the principle thereof; with said description being provided on an example basis and given in reference to the attached drawing, in which:

FIG. 1 is a skeleton diagram of a first analyzing device according to the invention;

FIG. 2 is a skeleton diagram, analogous to that in FIG. 1, of a second device according to the invention.

DETAILED DESCRIPTION OF THE PREFERRED EMBODIMENTS

With reference more specifically to FIG. 1, the device for analyzing the alcohol content of a gas comprises a conduit (11), endowed with a restriction (12), in which gas is caused to circulate (in other words, the subject being tested is made to blow into the widest nozzle (13) of this conduit), a pumping device (14), controlled by an electromagnet (15) with moving element (16) and means (17) to control the activation of the electromagnet (15). The pumping device (14) comprises an intake opening (18), into which a nozzle (19) branching from the conduit fits in a sealed manner, and a measurement chamber (20), one wall of which is constituted of an elastic membrane (21) or similar structure.

A closing element (22) connected to a piston (23) prevents air from flowing between the opening (18) and the measurement chamber (20). This closing element (22) is connected to a piston (23) cooperating with the elastic membrane (21). Before use, the piston (23) is blocked by the moving element (16) into a position such that the membrane (21) is distorted and kept in a position for which the volume of the measurement chamber (20) is at a minimum. Means to detect and measure alcohol are housed in the chamber (20). For example, this can involve an electrochemical cell (25) which is known in and of itself, sending an electrical signal which is representative of the quantity of alcohol introduced with the air in the chamber (20), when the moving element (16) moves aside and frees the membrane (21). The movement of the latter causes the predetermined volume of the chamber (20) to increase, thus causing a predetermined value of exhaled air to be taken into the conduit (11).

According to an important characteristic of the invention, the activation control means (17) comprise a cascade assembly of a device (27) which is sensitive to the pressure which prevails in the conduit (11) and a volume evaluation device (28), controlled by the pressure sensitive device (27). In the example in FIG. 1, the device (27) is a proportional device sensor, whose pneumatic intake (29) is connected to the opening (18) upstream from the closing element (22). Such a sensor could, for example, be a 130 PC type piezo-resistive sensor marketed by the Honeywell company. The electrical outlet (30) of this sensor is connected to the input of the evaluation device (28) which, in the same example in FIG. 1, is comprised essentially of an integration circuit and a threshold validation circuit, issuing a validation signal at the outlet (31) when the signal issued by said integration circuit has reached a predetermined value. Thus, the signal issued by the proportional sensor (27) is representative of the flow of the air blown into the conduit (11) and the integration circuit receives this signal and issues a signal which is representative of the total volume of exhaled air such that the validation signal appears at the outlet (31) only when a minimum volume of air has been exhaled.

Moreover, the device is endowed with means to detect a low threshold of the pressure prevailing in the conduit (11).

In the example in FIG. 1, advantageous use is made of the presence of the proportional sensor (27) whose outlet (30) is connected to the input of a threshold circuit (35). The outlet (36) of the threshold circuit (35) thus issues another validation signal. The outlets (31) and (36) are connected to the corresponding inputs for logical equipment (38) producing at the outlet thereof (39) a control signal for the electromagnet (15) at least when the evaluation device (28) and the low threshold detection device (35) have produced their respective validation signals. In other terms, the logical equipment (38) essentially fulfills an ET function based on signals applied to the two inputs. They also comprise a third input which is connected to the outlet of a testing circuit (41) for the main operational parameters of the system (feed voltage, return to zero of the cell (25) outlet signal, cell temperature, locking of the pumping device, etc . . . ). Finally, the device described is endowed with a signaling device (40), for example, by means of sound, which is directly connected to the outlet (30). The device operates as follows. Before use and at the beginning of the test, the tripping of the electromagnet (15) is in any event prevented by the state of the outlet (31), at least as long as a mininum volume of air has not been exhaled into the tube (11). Moreover, as soon as use has begun, the pressure in the tube (11) exceeds the low threshold established by the circuit (35) such that the corresponding validation signal is not present at the outlet (36) as long as the subject being tested has not exhaled completely, after which the pressure in the conduit (11) drops again near the level of atmospheric pressure. During the entire testing procedure, the signal means (40) issues a continuous signal (for example, by means of sound) to ensure that the subject being tested has not inhaled fresh air in order to alter the measurement.

In the example in FIG. 2, the identical elements bear the same numeric references and will not be described again. In this example, the pressure sensitive means consist of an all-or-nothing type device (45), comprising, for example, a simple electromechanical contact which closes as soon as the low pressure threshold is exceeded. Under these conditions, the aforementioned evaluation equipment can be summarized as a simple inhibition device (46) which is activated by the sensor (45) and sends its validation signal after a predetermined period of time has lapsed. For example, it is assessed that an inhibition of one and one-half seconds is appropriate in most cases. Of course, the pressure threshold is detected by the simple change in state of the electromechanical contact associated with the sensor (45) such that the outlet of the latter is connected to an input for the logical equipment (38), for example, through the intermediary of an reversing switch (47). Operation is comparable to that of the device in FIG. 1, with the activation of the pumping device able to occur only after the exhalation is completed, when the pressure in the conduit (11) is again close to atmospheric pressure and the sensor (45) returns to its resting position.

According to an additional variation, the devices shown in FIGS. 1 and 2 can be supplemented by a commonly used device preventing any additional inhalation of air during the testing operation. This equipment (not shown) can, for example, be a valve, flap or ball, at the end of the conduit (11) opposite the widest nozzle (13), allowing only the exit of air at this level.

What is claimed is:

1. Device for analyzing the alcohol content of a gas, especially for testing an individual's alcoholemia level, comprising a conduit (11) for the circulation of said gas, a controlled pumping device (14) which is connected to said conduit to take in a first predetermined volume of said gas when it is activated, with said pumping device being associated with means (25) to detect and measure alcohol and means (17) for controlling the activation of the pumping device, characterized in that said means for controlling comprises a cascade assembly of a device (27) which is sensitive to the pressure which prevails in said conduit and an evaluation device (28), responsive to said pressure sensitive device, for evaluating a second volume of gas, wherein said means for controlling is adapted for activating said pumping device only when said second volume of gas has been evaluated.

2. Device according to claim 1, characterized in that said pressure sensitive device (27) is a proportional pressure sensor, which sends an electrical outlet signal representative of the flow of gas in said conduit, in that said evaluation device (28) comprises a circuit for issuing a signal representative of a volume of gas having passed through said conduit and a validation device for emitting a validation signal (31) when said signal representative of a volume reaches a predetermined value corresponding to said second volume.

3. Device according to claim 1, characterized in that said pressure sensitive device is an all-or-nothing pressure sensor (45) and in that said evaluation device comprises an inhibition device (46) activated by said sensor.

4. Device according to claim 3, characterized in that said pressure sensor comprises an electromechanical contact activated beyond a predetermined pressure threshold and controlling said inhibition device.

5. Device according to claim 2, characterized in that said means to detect a low pressure threshold comprises said proportional pressure sensor (27) and a threshold circuit (35) controlled by said proportional pressure sensor.

6. Device according to claim 3, characterized in that said means to detect a low pressure threshold comprise said all or nothing type pressure sensor (45).

7. Device according to claim 5, characterized in that the aforementioned logical means are also coupled to a surveillance circuit (41) for certain operational parameters.

8. Device according to claim 1, characterized in that it comprises a signaling device (40), for example, by means of sound, connected so that it can be controlled by the outlet of said pressure sensitive device.

9. Device according to claim 1, characterized in that it comprises a device such as a valve, flap or ball, at the end of the conduit (11) opposite the nozzle (13) preventing any additional inhalation of air.

10. Device according to claim 2, characterized in that said circuit comprises an integration circuit.

11. Device according to claim 6, characterized in that the aforementioned logical means are also coupled to a surveillance circuit (41) for certain operational parameters.

12. Device according to one of claims 1-4, 5-8 or 11, characterized in that it comprises means (30, 35) to detect a low threshold of the pressure prevailing in said conduit and logical means (38) issuing a control signal for said pumping system at least when said evaluation device and said low pressure threshold detection device have issued respective validation signals.

* * * * *